US010662240B2

(12) United States Patent
Ahlborg et al.

(10) Patent No.: US 10,662,240 B2
(45) Date of Patent: May 26, 2020

(54) COMPOSITION, KIT AND METHOD FOR INHIBITION OF IL-21 MEDIATED ACTIVATION OF HUMAN CELLS

(71) Applicant: MABTECH AB, Nacka Strand (SE)

(72) Inventors: Niklas Ahlborg, Nacka Strand (SE);
Staffan Paulie, Saltsjö-Duvnäs (SE)

(73) Assignee: MABTECH AB, Nacka Strand (SE)

( * ) Notice: Subject to any disclaimer, the term of this patent is extended or adjusted under 35 U.S.C. 154(b) by 0 days.

(21) Appl. No.: 15/537,566

(22) PCT Filed: Dec. 15, 2015

(86) PCT No.: PCT/EP2015/079794
§ 371 (c)(1),
(2) Date: Jun. 19, 2017

(87) PCT Pub. No.: WO2016/096858
PCT Pub. Date: Jun. 23, 2016

(65) Prior Publication Data
US 2018/0171010 A1    Jun. 21, 2018

(30) Foreign Application Priority Data

Dec. 19, 2014  (SE) ..................... 1451620

(51) Int. Cl.
C07K 16/24       (2006.01)
A61K 39/395      (2006.01)
A61K 39/00       (2006.01)

(52) U.S. Cl.
CPC ........ C07K 16/244 (2013.01); A61K 39/3955 (2013.01); A61K 2039/507 (2013.01); C07K 2317/76 (2013.01)

(58) Field of Classification Search
CPC ............... A61K 2300/00; A61K 45/06; A61K 39/3955; A61K 38/00; A61K 38/19; C07K 2317/76; C07K 2317/24; C07K 16/468; C07K 2317/64; C07K 2317/21; C07K 2317/51; C07K 16/22; C07K 2317/31; C07K 16/245; C07K 2317/56; C07K 16/34; C07K 16/241; C07K 2317/90; C07K 2317/567; G01N 2333/515; G01N 33/88; G01N 2333/48; G01N 2333/5443; Y10S 435/81; Y02A 50/412; Y02A 50/41; Y02A 50/401
See application file for complete search history.

(56) References Cited

U.S. PATENT DOCUMENTS 8,361,471 B2    1/2013  Kedl et al.
9,388,241 B2    7/2016  Sivakumar et al.
2007/0122413 A1 5/2007  Sivakumar et al.

FOREIGN PATENT DOCUMENTS

EP      0969866 B2         2/2009
WO      WO-2006/057027 A1  6/2006
WO      WO-2009/047360 A1  4/2009
WO      WO-2010/055366 A2  5/2010

OTHER PUBLICATIONS

Huang et al, Journal of Immunological Methods, available online on Dec. 15, 2014; vol. 417, pp. 60-66.*
Maurer et al, MAbs. 2012, vol. 4, No. 1, pp. 69-83.*
Spolski et al; Annual Review of Immunology; 2008. vol. 26, pp. 57-79.*
Jenny Huang et al., "ELISpot and EISA analyses of human IL-21-secreting cells: Impact of blocking IL-21 interaction with cellular receptors," Journal of Immunological Methods, 2015, pp. 60-66, vol. 417, XP029199034, available online Dec. 15, 2014.
Roberta Caruso et al., "A Functional Role for Interleukin-21 in Promoting the Synthesis of the T-Cell Chemoattractant, MIP-3a, by Gut Epithelial Cells," Gastroenterology, Jan. 2007, pp. 166-175, vol. 132, No. 1, XP005920672.
Mark F. Maurer et al., "Generation and characterization of human anti-human IL-21 neutralizing monoclonal antibodies," MABS, Landes Bioscience, US, Jan. 2012, pp. 69-83, vol. 4, No. 1, XP009159604.
Cañete et al., 2014, "Efficacy and Safety of NNC0114-006, an Anti-IL-21 Monoclonal Antibody, in Patients with Active Rheumatoid Arthritis,"ACR/ARHP Annual Meeting, Abstract No. 947.
Hippen et al., 2012, "Blocking IL-21 signaling ameliorates xenogeneic GVHD induced by human lymphocytes,"Blood, 119(2):619-28. doi: 10.1182/blood-2011-07-368027. Epub Nov. 10, 2011.
Lewis et al., "Anti-IL-21 monoclonal antibody reduces disease severity and inflammatory cytokines in a murine model of psoriasis and colitis," J Immunol, 182(1 Supplement) 97:16 (Abstract), 2009.
Niu et al., 2013, "IL-21 and Related Diseases," J Clin Cell Immunol, S1:008. doi:10.4172/2155-9899.S1-008.

* cited by examiner

Primary Examiner — Bridget E Bunner
Assistant Examiner — Fozia Hamud
(74) Attorney, Agent, or Firm — Faegre Drinker Biddle & Reath LLP

(57) ABSTRACT

A synergistic composition, kit and method for inhibition and/or neutralization of IL-21 mediated activation of human cells including (i) a first agent being an antibody or antibody fragment thereof directed to a first epitope of IL-21, and (ii) a second agent being an antibody or antibody fragment thereof directed to a second epitope of IL-21 is disclosed. The inhibition and/or neutralization of IL-21 mediated activation of human cells is for use in the prophylaxis and/or treatment of disease of immune-related conditions including inflammatory disease, autoimmunity and lymphomas.

20 Claims, 6 Drawing Sheets

Figure 1:
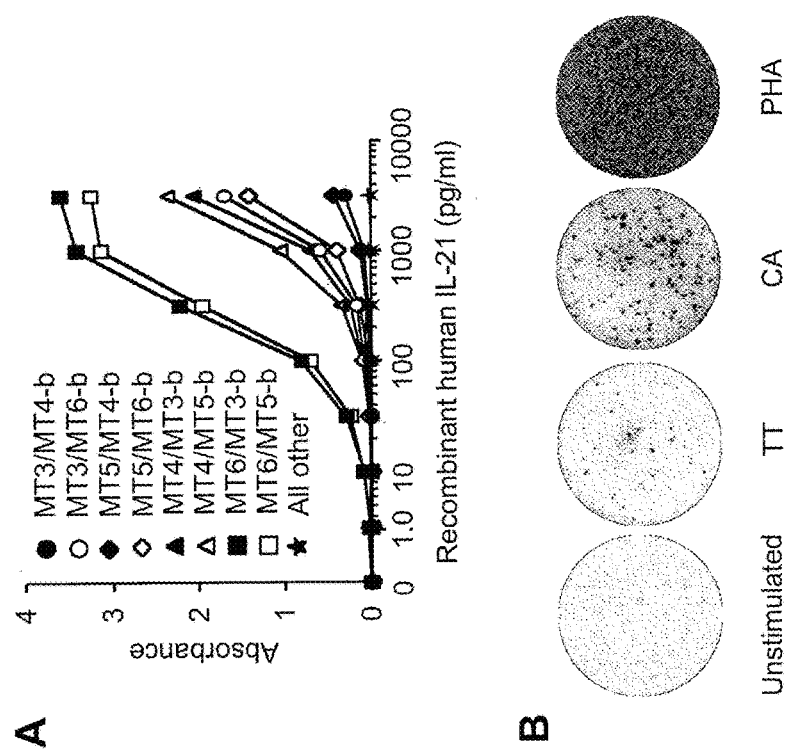

COMPOSITION, KIT AND METHOD FOR INHIBITION OF IL-21 MEDIATED ACTIVATION OF HUMAN CELLS

CROSS-REFERENCE TO PRIOR APPLICATIONS

This application is a § 371 National Stage Application of PCT International Application No. PCT/EP2015/079794 filed Dec. 15, 2015, which claims priority to Swedish Application No. 1451620-7 filed Dec. 19, 2014, each of which are herein incorporated by reference in their entirety.

TECHNICAL FIELD

The present invention relates to a synergistic composition, kit and method for inhibition and/or neutralization of IL-21 mediated activation of human cells by using (i) a first agent being an antibody or antibody fragment thereof directed to a first epitope of IL-21, and (ii) a second agent being an antibody or antibody fragment thereof directed to a second epitope of IL-21. The inhibition and/or neutralization of IL-21 mediated activation of human cells is for use in the prophylaxis and/or treatment of disease of immune-related conditions including inflammatory disease, autoimmunity and lymphomas.

BACKGROUND OF THE INVENTION

Interleukin (IL)-21 is an important regulatory cytokine with impact on both innate and adaptive immune cells. It is mainly produced by activated CD4+ T cells, follicular T-helper cells (Th) and natural killer T cells (Leonard et al., 2008) and targets a number of IL-21 receptor-expressing cells, primarily B, T and NK cells but also macrophages and dendritic cells (Spolski and Leonard, 2008). The IL-21 receptor is comprised of an IL-21-specific receptor chain (IL-21Rα) and the common gamma chain (CD132) that is shared by the receptors for IL-2, IL-4, IL-7, IL-9 and IL-15 (Spolski and Leonard, 2008). Important biological effects of IL-21 include the induction of T-cell differentiation into Th17 cells that produce IL-17A and also contributes to IL-21 production (Korn et al., 2007), enhanced proliferation and cytotoxic activity of CD8+ T cells (Liu et al., 2007), functional maturation of NK cells (Brady et al., 2010) and activation of monocytes (Vallières and Girard, 2013). In concert with other cytokines and signaling molecules, IL-21 also regulates the development and activation of B cells into Ig-secreting cells (Ozaki et al., 2004; Moens and Tangye, 2014).

Due to its importance as a regulatory cytokine, an aberrant production of IL-21 may also have pathogenic consequences, and studies in mice have demonstrated its potential involvement in a variety of immune-related conditions including inflammatory disease and autoimmunity (Ozaki et al., 2004; Vinuesa et al., 2005; Vogelzang et al., 2014). In humans, T cells producing IL-21 have been shown to be increased in patients with systemic lupus erythematosus, coinciding with a similar increase in IL-17A producing T cells (Dolff et al., 2011), in rheumatoid arthritis (Ma et al., 2012) and in celiac disease (van Leeuwen et al., 2013). Furthermore, there is evidence for IL-21 serving as a potential tumorigenic factor in certain lymphomas (Lamprecht et al., 2008; van der Fits et al., 2012) but, IL-21 also has the capacity to induce apoptosis in other lymphomas (Akamatsu et al., 2007; Gelebart et al., 2009).

Granted patents relating to medical uses of known antibodies (such as anti-CD22) directed to an epitope on a molecule are known in the art. An example is EP0969866 B2 wherein neither the amino acid sequence of the anti-CD22 antibody, nor the sequence of residues on CD-22 molecule, are disclosed. However, to our knowledge, prior art documents are silent about medical uses (as well as compositions, kits and methods of treatments thereof) antibodies with different specificities for the treatment IL-21.

Consequently, there is a need to inhibit and/or neutralize IL-21 mediated activation of human cells for the prophylaxis and/or treatment of the above mentioned diseases and conditions.

OBJECT OF THE INVENTION

The first object of the invention is to provide a synergistic composition for inhibition and/or neutralization of IL-21 mediated activation of human cells.

The second object of the invention is to provide a synergistic kit for inhibition and/or neutralization of IL-21 mediated activation of human cells.

The third object of the invention is to provide a synergistic method of inhibition and/or neutralization of IL-21 mediated activation of human cells.

SUMMARY OF INVENTION

The first object of the invention is attained by an embodiment which is a synergistic composition comprising (i) first agent being an antibody or antibody fragment thereof directed to a first epitope of IL-21, and (ii) a second agent being an antibody or antibody fragment thereof directed to a second epitope of IL-21, for use in the prophylaxis and/or treatment of disease, wherein said composition is formulated in a pharmaceutically acceptable excipient, and wherein the combined administering of said first and second agents has a synergistic neutralizing effect on IL-21 activation of cells.

A more efficient blocking of IL-21 may lead to a better therapeutic effect of the treatment of diseases associated with 1-21. Moreover, the more efficient blocking may permit treating with a lower dose of antibody. Apart from a significant economic advantage (lower cost of production), treatment with a lower dose can potentially also reduce problems with immunogenicity. Induction of anti-drug antibodies (ADA) is a significant problem when using protein drugs, such as antibodies, as ADAs may result in neutralization of the therapeutic effect and even in an immunological overreaction (anaphylaxis) to the drug. ADAs are often directed to the active site of the antibody, neutralizing its capacity to bind to its target. The reason for induction of ADAs is not always clear but the active site of an antibody represents a unique structure that may be recognized as foreign by the body. The administration of lower amounts of antibody may make induction of ADAs less likely. Even with the same total dos-age, the concentration of the unique structure represented by the active site would only be half of that when giving a single antibody since each anti-IL-21 antibody has a separate distinct active site.

A further embodiment relates to a composition, wherein the first agent is anti-IL-21 antibody or antibody fragment thereof, and/or wherein the second agent is anti-IL-21 antibody or antibody fragment thereof. Preferably the first agent is anti-human IL-21 antibody or antibody fragment thereof. Preferably the second agent is anti-human IL-21 antibody or antibody fragment thereof.

A further embodiment relates to a composition, wherein (i) said first agent is has the specificity of MT6 antibody or antibody fragment thereof, and (ii) said second agent has the specificity of MT3 antibody or antibody fragment thereof. The combined use of a first agent having the specificity of MT6 and a second agent having the specificity of MT3, or fragments thereof, has a strong synergistic neutralizing effect on IL-21 activation of cells.

A further embodiment relates to a composition wherein (i) said first agent is MT6 (for example MT216G) antibody or antibody fragment thereof, and (ii) said second agent is MT3 (for example MT21.3m) antibody or antibody fragment thereof. The combined use of MT6 and MT3 antibodies, or fragments thereof, has a strong synergistic neutralizing effect on IL-21 activation of cells.

A further embodiment relates to a composition, wherein (i) said first agent is has the specificity of MT6 antibody or antibody fragment thereof, and (ii) said second agent has the specificity of MT5 antibody or antibody fragment thereof. The combined use of a first agent having the specificity of MT6 and a second agent having the specificity of MT5, or fragments thereof, has a strong synergistic neutralizing effect on IL-21 activation of cells.

A further embodiment relates to a composition, wherein (i) said first agent is MT6 (for example MT216G) antibody or antibody fragment thereof, and (ii) said second agent is mt5 antibody or antibody fragment thereof.

A further embodiment relates to a composition wherein said first and/or second agent is a monoclonal antibody (mAb), preferably said mAb carries one specificity. The advantage of using monoclonal antibodies is that they bind to one epitope on an antigen while polyclonal antibodies recognize multiple epitopes on any one antigen. Moreover, the production of monoclonal antibodies gives rise to a large amount of specific antibodies while the production of polyclonal antibodies gives rise to large amount of non-specific antibodies.

A further embodiment relates to a composition wherein said first and second agents is in the form of a bispecific antibody (bisAb), or fragment thereof, being able to bind both the first and second epitopes of IL-21. A bispecific antibody can be designed to bind either two adjacent epitopes on a single antigen molecule, thereby increasing avidity, or to bind two separate antigen molecules. Hence, this embodiment opens up for treatment with bi-functional antibodies, i.e. antibodies carrying each of the two specificities in the same molecule, if this is found more efficient or more desirable from a production aspect.

A further embodiment relates to a composition wherein said first and/or second agent is a Fab fragment, F(ab')2 fragment, single chain Fv fragment or monovalent IgG. Antibody fragments retain the targeting specificity of whole mAbs but can be produced more economically and possess other unique and superior properties for therapeutic applications.

A further embodiment relates to a composition wherein said first and/or second agent comprises a chimeric antibody or a fragment of a chimeric antibody. Chimeric antibodies have reduced immunogenicity when compared to murine antibodies and are produced by genetic engineering to generate chimeric antibodies containing human constant domains and the mouse variable domains to retain specificity.

A further embodiment relates to a composition wherein said first and/or second agent comprises a humanized antibody or a fragment of a humanized antibody. Humanized antibodies have reduced immunogenicity when compared to chimeric antibodies and are engineered by the grafting of CDRs from a mouse antibody onto a human variable region framework.

A further embodiment relates to a composition wherein said first and/or second agent comprises a fully human antibody or a fragment of a fully human antibody. The use of fully human antibodies may lead to reduced immunogenicity in comparison with chimeric and humanized antibodies and fragments thereof.

A further embodiment relates to a composition, comprising a first agent being an antibody or antibody fragment thereof directed to a first epitope of IL-21, wherein said first epitope comprises the third helical region interacting with the IL-21 receptor chain as well as the last helical region that interacts with the common gamma chain, wherein said first agent is an anti-IL-21 antibody or antibody fragment thereof, preferably said first agent has the specificity of MT6 antibody or antibody fragment thereof, more preferably said first agent is MT6 antibody or antibody fragment thereof, most preferably said first agent is MT216G antibody or antibody fragment thereof.

A further embodiment relates to a composition, comprising a second agent being an antibody or antibody fragment thereof directed to a second epitope of IL-21, wherein said second epitope comprises the β-strand region (D), wherein said second agents is an anti-IL-21 antibody or antibody fragment thereof, preferably said second agent has the specificity of MT3 antibody or antibody fragment thereof, more preferably said second agent is MT3 antibody or antibody fragment thereof, most preferably said second agent is MT21.3m antibody or antibody fragment thereof.

A further embodiment relates to a composition for use in the prophylaxis and/or treatment of disease. This allows prophylaxis and/or treatment of diseases associated with aberrant production of IL-21.

A further embodiment relates to a composition for use in the prophylaxis and/or treatment of diseases of immune-related conditions including inflammatory disease, autoimmunity and lymphomas. This allows prophylaxis and/or treatment of inflammatory disease, autoimmunity and lymphomas associated with aberrant production of IL-21.

A further embodiment relates to a composition wherein said immune-related conditions including inflammatory disease and autoimmunity are selected from the group comprising systemic lupus erythematosus, rheumatoid arthritis, celiac disease, osteoarthritis, psoriatic arthritis, ankylosing spondylitis, transplant rejection, inflammatory bowel disease, psoriasis, cystic fibrosis and Crohn's disease. This allows prophylaxis and/or treatment of systemic lupus erythematosus, rheumatoid arthritis, celiac disease, osteoarthritis, psoriatic arthritis, ankylosing spondylitis, transplant rejection, inflammatory bowel disease, psoriasis, cystic fibrosis and Crohn's disease, which are diseases associated with aberrant production of IL-21.

A further embodiment relates to a composition wherein the first and second agents are administered simultaneously and/or sequentially.

A further embodiment relates to a composition wherein the subject is human.

The second object of the invention is attained by an embodiment which is a synergistic kit for inhibition and/or neutralization of IL-21 mediated activation of human cells comprising (i) a first agent being an antibody or antibody fragment thereof directed to a first epitope of IL-21, and (ii) a second agent being an antibody or antibody fragment thereof directed to a second epitope of IL-21, for use in the prophylaxis and/or treatment of disease, wherein said composition is formulated in a pharmaceutically acceptable excipient, wherein the first and second agents are administered simultaneously or sequentially, and wherein the combined administering of said first and second agents has a synergistic neutralizing effect.

Further embodiments of the second object of the invention comprise the first and the second agents which are defined in the above described embodiments of the first object of the invention.

Further embodiments of the second object of the invention relate to the diseases defined in the above described embodiments of the first object of the invention.

The third object of the invention is attained by a preferred embodiment which is a method of inhibition and/or neutralization of IL-21 mediated activation of human cells comprising the steps of administering (i) a first agent being an antibody or antibody fragment thereof directed to one epitope of IL-21, and (ii) a second agent being an antibody or antibody fragment thereof directed to a second epitope of IL-21, for use in the prophylaxis and/or treatment of disease, wherein said administration is simultaneous or sequential, wherein the combined administering of said first and second agents has a synergistic neutralizing effect on IL-21 activation of cells.

Further embodiments of the third object of the invention comprise the first and the second agents which are defined in the above preferred embodiments of the first object of the invention.

Further embodiments of the third object of the invention relate to the diseases defined in the above preferred embodiments of the first object of the invention.

The present invention further relates to a composition for non-medical use wherein said composition comprises (i) a first agent being an antibody or antibody fragment thereof directed to a first epitope of IL-21, and (ii) a second agent being an antibody or antibody fragment thereof directed to a second epitope of IL-21. The first and second agents are the same as the ones disclosed in the above preferred embodiments of the first object of the invention.

The present invention further relates to a kit for non-medical use wherein said kit comprises (i) a first agent being an antibody or antibody fragment thereof directed to a first epitope of IL-21, and (ii) a second agent being an antibody or antibody fragment thereof directed to a second epitope of IL-21. The first and second agents are the same as the ones disclosed in the above preferred embodiments of the second object of the invention.

FIGURES

FIG. 1. Functionality of mAbs to human IL-21 in ELISA and ELISpot. A) Four mAbs (MT3-MT6) reactive with rhIL-21 were tested in all possible capture and detection mAb combinations in ELISA using rhIL-21 as analyte. The detection mAbs were biotinylated (–b). Non-functional combinations are shown as "All other". B) The combination of capture mAb MT6 and biotinylated detection mAb MT3 was evaluated in ELISpot. Shown are images obtained with $5\times10^5$ PBMC/well (from one donor) incubated without stimuli or with Tetanus Toxoid (TT), *Candida albicans* extract (CA) or Phytohemagglutinin (PHA).

Figure 2:
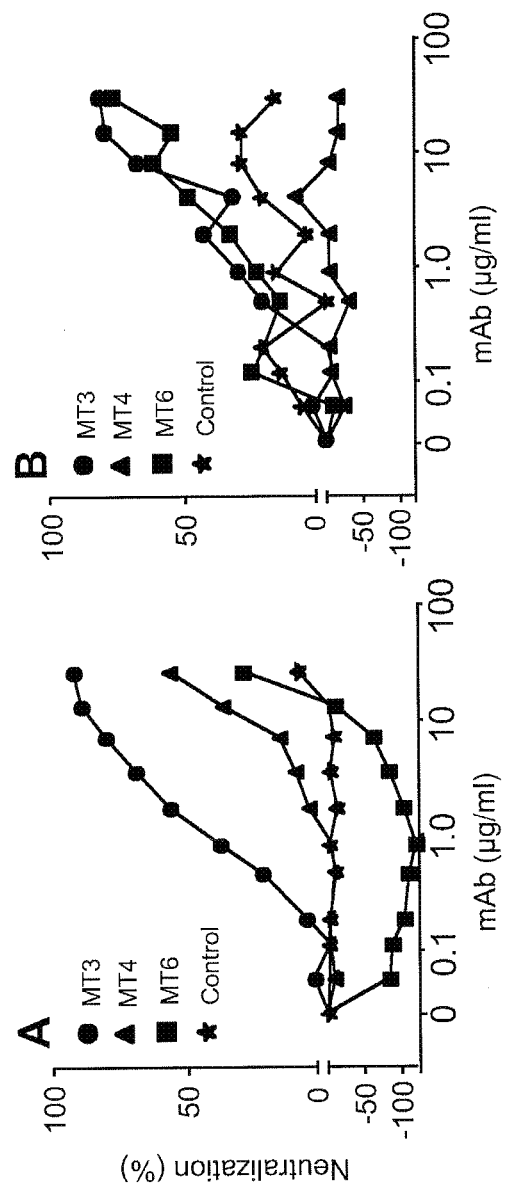

FIG. 2. Neutralizing capacity of mAbs to IL-21. A) Neutralization assay using HEK cells transfected with plasmids encoding the IL-21 activation pathway and secreted alkaline phosphatase as a reporter. The cells were stimulated with rhIL-21 with or without serial dilutions of anti-IL-21 mAbs MT3, MT4, MT6 and an isotype/subclass matched control mAb (all mAbs are IgG1 κ). Following incubation for 20 h, enzyme activity in supernatants was measured. Data shown is the mean of two experiments. B) Neutralization assay using human PBMC incubated for 4 days with rhIL-21 in the presence of mAbs followed by detection of IgG-secreting B cells by ELISpot. The data shown is the mean of results from two PBMC donors. rhIL-21-induced B-cell responses in the absence of mAbs was 75 and 140 spots/200,000 PBMC and spontaneous B cells secreting IgG without rhIL-21 yielded <5 spots/200,000 PBMC. PBMC from an additional 10 donors yielded similar results when IgG levels were measured by ELISA after incubation with rhIL-21+/–mAbs (not shown).

Figure 3:
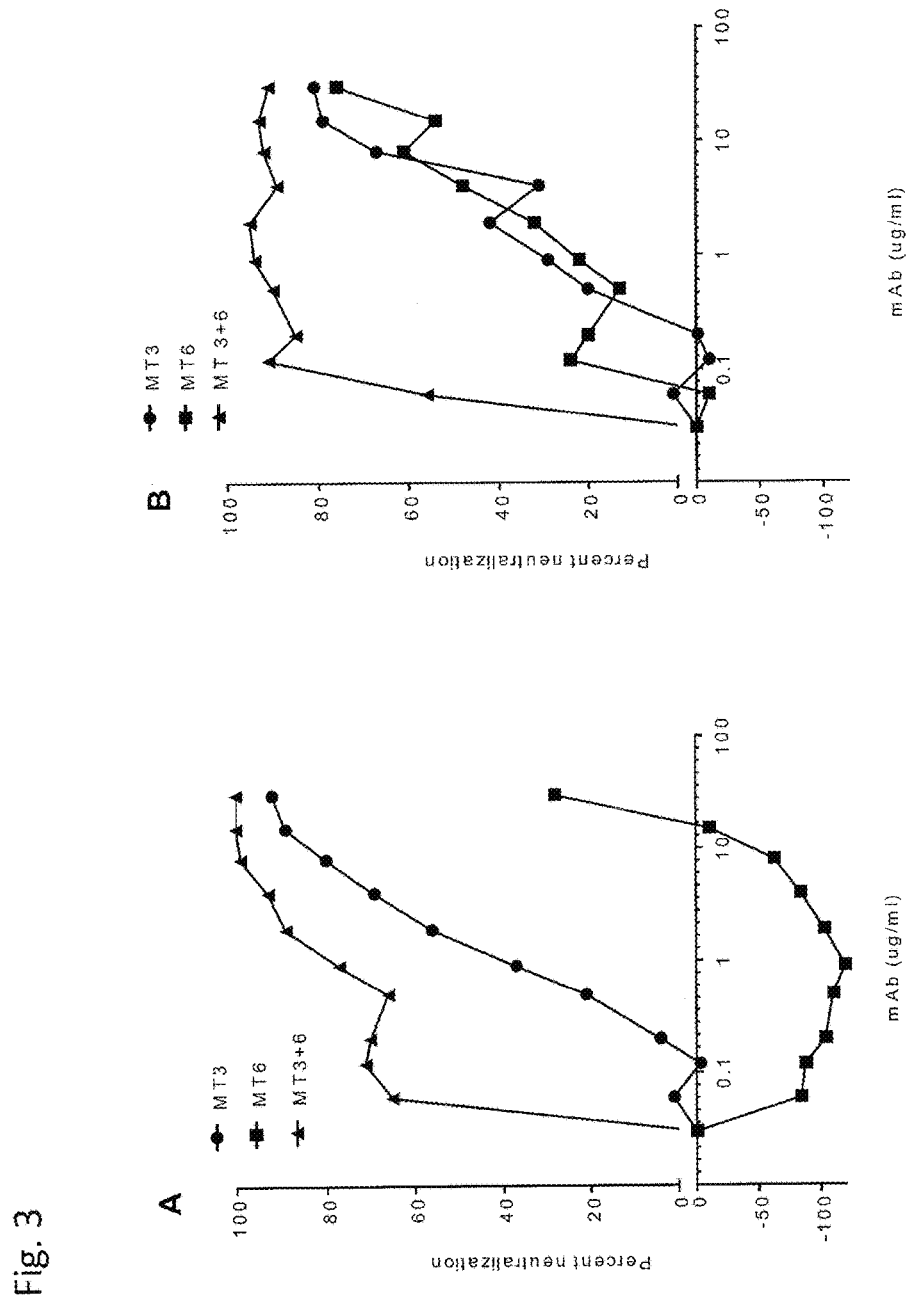

FIG. 3 A) HEK cells transfected with plasmids encoding the IL-21 activation pathway and secreted alkaline phosphatase as a reporter were stimulated with IL-21 with or without the monoclonal antibodies MT3 and MT6 alone or in combination (MT3+MT6). Following incubation for 20 h, enzyme activity in supernatants was measured. Data shown is the mean of two experiments.

B) Human PBMC were incubated for 4 days with rhIL-21 in the presence of the monoclonal antibodies (mAbs) MT3 and MT6 alone or in combination (MT3+MT6) followed by detection of IgG-secreting B cells by ELISpot. The data shown is the mean of results from two PBMC donors. RhIL-21-induced B-cell responses in the absence of antibodies gave 75 and 140 spots/200,000 PBMC in the respective donor and spontaneous B cells secreting IgG without rhIL-21 yielded <5 spots/200,000 PBMC. PBMC from an additional 10 donors produced similar results when IgG levels were measured by ELISA after incubation with rhIL-21+/–mAbs (not shown).

Figure 4:
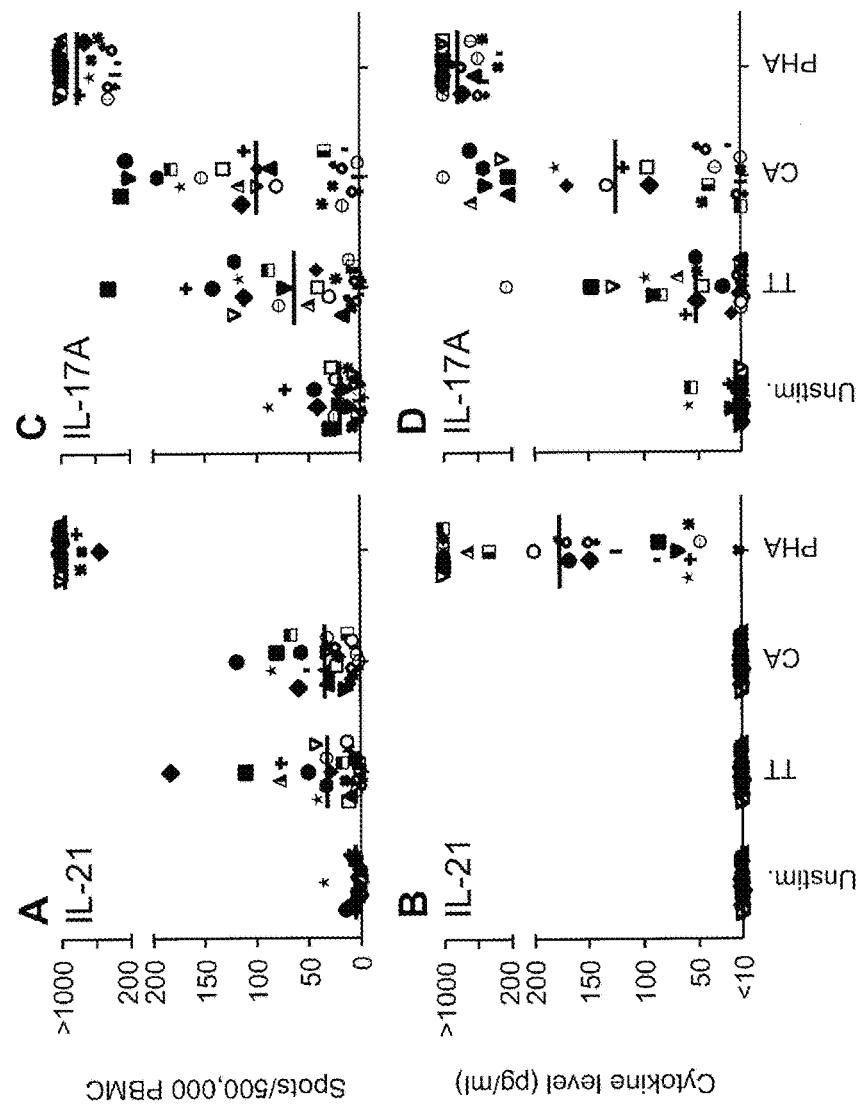

FIG. 4. ELISA and ELISpot analysis of IL-17A and IL-21 secretion by ex vivo-stimulated PBMC. PBMC from 24 healthy subjects were incubated for 40 h in IL-21 (A) and IL-17A (C) ELISpot wells or in vials for subsequent analysis of supernatants by IL-21 (B) and IL-17A (D) ELISA. Unstimulated, antigen-stimulated (*Candida albicans*, CA; Tetanus toxoid, TT) and Phytohemagglutinin (PHA)-stimulated cells were used at $5\times10^6$ PBMC/ml. Spots/well exceeding 1000 spots/well were set to >1000 spots/well. IL-21 levels in ELISA exceeding 1000 pg/ml are shown as >1000 pg/ml. The lowest detection limit of the ELISAs was set to 10 pg/ml. Each symbol represents PBMC from one individual.

Figure 5:
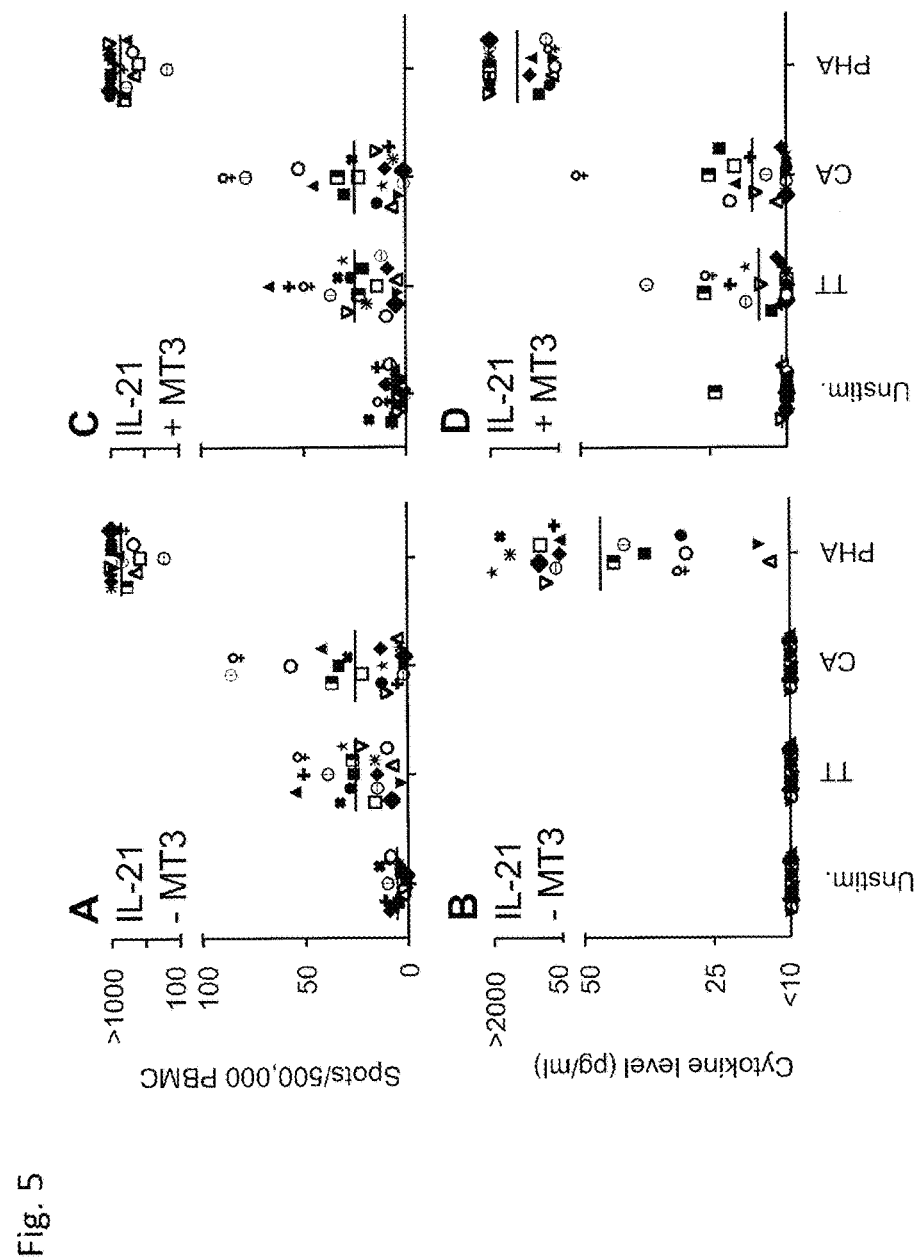

FIG. 5. ELISA and ELISpot analysis of IL-21 secretion by ex vivo-stimulated PBMC cultured with or without a neutralizing/blocking anti-IL-21 mAb MT3. PBMC from 18 healthy subjects were incubated for 40 h in ELISpot wells or in vials for subsequent analysis of supernatants by ELISA. Unstimulated, antigen-stimulated (*Candida albicans*, CA; Tetanus toxoid, TT) and (Phytohemagglutinin) PHA-stimulated cells were used at $5\times10^6$ PBMC/ml. The IL-21 ELISpot (A & C) and ELISA (B & D) were used to analyze PBMC cultured without mAb MT3 (A & B) or PBMC cultured in the presence of 1 µg/ml of mAb MT3 (B & D). Spots/well exceeding 1000 were set to >1000 spots/well. IL-21 levels in ELISA exceeding 1000 pg/ml are shown as >1000 pg/ml. The lowest detection limit of the ELISAs was set to 10 pg/ml. Each symbol represents PBMC from one individual.

Figure 6:
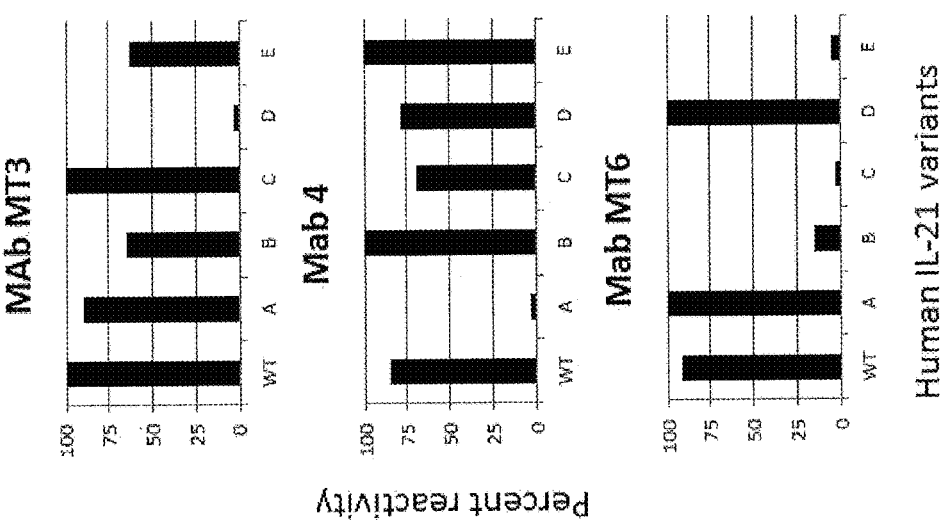

FIG. 6. Epitope mapping of three mAbs to human IL-21 using chimeric human-mouse IL-21 constructs. MAb MT3, 4 and MT6 were analyzed by ELISA for their reactivity with human wild-type (WT) IL-21 as well as five chimeric human-mouse IL-21 constructs designated A-E. The Y-axis shows percent of reactivity for each mAb's reactivity with the six IL-21 variants. The percent of reactivity was calculated by dividing the absorbance value obtained at a given dilution of each chimera with the absorbance value obtained with the mAb yielding the highest reactivity with the same chimera, followed by multiplication with 100. Since the three mAbs display a very comparable reactivity with IL-21 WT, a loss of reactivity with a chimera displayed by a mAb suggests that the chimera comprises residues of importance for the mAb's epitope.

DETAILED DESCRIPTION

The present invention relates to a synergistic composition, kit and method for inhibition and/or neutralization of IL-21 mediated activation of human cells comprising (i) first agent being an antibody or antibody fragment thereof directed to a first epitope of IL-21, and (ii) a second agent being an antibody or antibody fragment thereof directed to a second epitope of IL-21.

The inhibition and/or neutralization of IL-21 mediated activation of human cells achieves the prophylaxis and/or treatment of diseases associated with aberrant production of IL-21. These diseases include a variety of immune-related conditions including inflammatory disease and autoimmunity. Specific examples are systemic lupus erythematosus, rheumatoid arthritis and celiac disease. Further examples are osteoarthritis, psoriatic arthritis, ankylosing spondylitis, transplant rejection, inflammatory bowel disease, psoriasis, cystic fibrosis and Crohn's disease. Additionally, there is evidence for IL-21 serving as a potential tumorigenic factor in certain lymphomas. Hence, the inhibition and/or neutralization of IL-21 mediated activation of human cells can also achieve prophylaxis and/or treatment of lymphomas.

The inhibition and/or neutralization of IL-21 mediated activation of human cells is attained by using two different antibodies, either simultaneously or sequentially, preferably simultaneously, more preferably said antibodies are combined in a composition.

In the present invention the term antibody refers to a full-length immunoglobulin molecule and encompasses any polypeptide comprising an antigen binding site. In a preferred embodiment the first and/or the second agents may be a monoclonal antibody. Such antibodies are monospecific antibodies, i.e. they all have affinity for the same antigen, and are made by identical immune cells that are all clones of a unique parent cell, in contrast to polyclonal antibodies which are made from several different immune cells. Monoclonal antibodies have monovalent affinity, in that they bind to the same epitope.

However, in further preferred embodiments, the first and/or second agents may be antibody fragments. The term antibody fragment refers to an immunologically active portion of an immunoglobulin molecule. Examples of antibody fragments are F(ab')2, Fab, scFv and monovalent IgG (Holliger et al., 2005). Regardless of structure, an antibody fragment binds to the same antigen that is recognized by the intact antibody. As an example, an anti-IL-21 monoclonal antibody fragment binds to an epitope of IL-21. Additionally, the term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

The first and/or second agents may in a further preferred embodiment be a chimeric antibody which refers to a recombinant protein that contains the variable domains including the complementarity determining regions (CDRs) of an antibody derived from one species, preferably a murine antibody, while the constant domains of the antibody molecule is derived from those of a fully human antibody (Jones et al., 1986; Vaughan T. J. et al., 1998).

A humanized antibody is a recombinant protein in which the CDRs from an antibody from one species; such as a murine antibody, is transferred from the heavy and light variable chains of the rodent antibody into human heavy and light variable domains. The first and/or second agents may be a humanized antibody in a further preferred embodiment. The constant domains of such an antibody molecule is derived from those of a fully human antibody (Winter G. et al., 1993).

The first and/or second agents may be a fully human antibody in a further preferred embodiment. A fully human antibody is referred to a genetically engineered antibody which is produced by (i) phage display, where a library of human antibodies is expressed on the surface of phage and subsequently selected and amplified in *E. coli*, and (ii) transgenic mice expressing a human antibody repertoire (Vaughan T. J. et al., 1998).

A pharmaceutical composition or kit comprising the first and second agents may be administered in a therapeutic effective amount via intravenous, intraperitoneal, intramuscular, intracavity, subcutaneous, oral, topical, transmucosal and transdermal routes of administration. The pharmaceutical compositions and formulations may comprise pharmaceutical excipients, which are compatible (i) with antibodies and/or antibody fragments, and/or (ii) pharmaceutical administration. The pharmaceutical formulations and excipients used in the art, and compatible with the composition, kit and method disclosed in the present invention, can be derived from the textbook Remington: The Science and Practice of Pharmacy (20$^{th}$ Edition and 19$^{th}$ Edition—Editor Gennaro).

Example 1—Inhibition and/or Neutralization of IL-21 Mediated Activation

This specific example relates to the inhibition and/or neutralization of IL-21 mediated activation of human cells by using (i) a first agent being MT6 (MT216G) directed to a first epitope of IL-21, and (ii) a second agent being MT3 (MT21.3m) directed to a second epitope of IL-21. The results indicate that when MT3 and MT6 antibodies are used together, they have a strong synergistic neutralizing effect on IL-21 activation of both HEK cells and PBMC.

Experimental Section

Generation of mAbs to Human IL-21

MAbs were made using methods described previously (Zuber et al., 2005). Briefly, hybridomas were generated using cells from BALB/c mice immunized with recombinant human (rh)IL-21 (Peprotech, Rockville Hill, N.J., USA). Mice were treated according to the guidelines of the Swedish Ethical Committee for Animal Protection. rhIL-21-reactive hybridomas were identified by ELISA; selected hybridomas were subcloned and mAbs were produced and purified on Protein G columns. A quantity of each mAb was biotinylated to allow its use as detection reagent. Finally, the mAbs were tested in capture and detection combinations to identify the optimal pair of mAbs for ELISA and ELISpot.

Four new mAbs with high reactivity with rhIL-21 were assessed for functionality as capture/detection pairs in ELISA. The combination of mAb MT6 (MT216G) for capture and mAb MT3-biotin for detection yielded a lowest detection limit of rhIL-21 below 10 pg/ml in ELISA which is comparable to other highly sensitive cytokine ELISAs utilizing the same amplification system (biotin-streptavidin) and enzymatic detection with colorimetric substrates (FIG. 1A). After confirming reactivity of the mAb pair with native IL-21 and functionality in the ELISpot assay (FIG. 1B), this combination was selected foe subsequent experiments. MAb MT5 was fully comparable to MT3 (MT21.3m) as detection mAb. MT6 and MT3 are also known as MT216G and MT21.3m, respectively (Mabtech). The monoclonal antibody MT3 (also called MT21.3m) is secreted by the hybridoma cell line designated MT21.3m which has been deposited under the provisions of the Budapest Treaty with the American Type Culture Center (ATCC), 10801 University Boulevard. Manassas, Va., 20110, USA, on Mar. 19, 2020 under Patent Deposit Number PTA-126045. The monoclonal antibody MT6 (also called MT216G) is secreted by the hybridoma cell line designated MT21.6G which has been deposited under the provisions of the Budapest Treaty with the American Type Culture Center (ATCC), 10801 University Boulevard, Manassas, Va., 20110, USA, on Mar. 19, 2020 under Patent Deposit Number PTA-126046. The monoclonal antibody MT5 is secreted by the hybridoma cell line designated MT21.5 which has been deposited under the provisions of the Budapest Treaty with the American Type Culture Center (ATCC), 10801 University Boulevard, Manassas, Va. 20110, USA, on Mar. 19, 2020 under Patent Deposit Number PTA-126568.

Preparation of Human PBMC

PBMC were isolated from buffy coats of anonymous healthy blood donors from Karolinska University Hospital (Solna, Sweden) and frozen as described (Mäkitalo et al., 2002). Before use, PBMC were thawed at 37° C., washed in culture medium (RPMI-1640 with 10% fetal calf serum, 2 mM L-glutamine, 100 IU/ml Penicillin, 100 μg/ml Streptomycin and 1 mM HEPES; Life Technologies, Glasgow, UK). After being rested for 1 h in a 37° C. incubator with 5% $CO_2$, PBMC were resuspended and aggregated cell debris was allowed to sediment during 1 minute. Following that, cells in suspension were moved to a new vial and PBMC were counted using a Guava EasyCyte mini (Millipore, Billerica, Mass., USA).

MAb Blocking of IL-21 Receptor Interaction with Transfected HEK Cells

Plasmids were produced by Genscript (Pisctaway, N.J., USA). Synthesized genes encoding, IL-21 receptor (Uniprot Q9HBE5), common gamma chain (Uniprot P31785), Janus Kinase 3 (Uniprot, P52333) and Signal transducer and activator of transcription 3 (Uniprot P40763) were cloned into plasmid pcDNA 3.1/Zeo (Life Technologies/Invitrogen, Carlsbad, Calif., USA). pGL4.52-SEAP-SIE-RE-Hygro STAT3 reporter plasmid was made by modifying plasmid pGL4.52-luc2P-STAT5-RE-Hygro (Promega, Madison, Wis., USA); a secreted alkaline phosphatase gene from the pSEAP2 vector U89937 (Clontech, Mountain View, Calif., USA) was used to replace the luc2P gene and the STAT5 response element was replaced with the STAT3 (SIE) response element from pGL4.47-luc2P-SIE-RE-Hygro (Promega). IL-21 responsive human embryonic kidney (HEK) 293T/17 cells (LGC AB, Borås, Sweden) were made by co-transfection with the above (five) plasmids. HEK 293T/17 cells were selected based on high transfectability, the cells constitutively express the simian virus 40 (SV40) large T antigen that permits episomal replication of plasmid pcDNA 3.1/Zeo, which contains a SV40 ori. Cell media and transfection reagents were from Life Technologies. Cells were selected in 6-well tissue culture plates at $1 \times 10^6$ cells/well in 2 ml DMEM medium with 10% fetal calf serum and cultured overnight at 37° C. with 5% $CO_2$. Cells were transfected with plasmids (0.5 g/plasmid) together with 5 μl Lipofectamine 2000 in Opti-MEM+GlutaMAX according to the manufacturer's instructions. After 20 h, cells were detached using 0.05% trypsin/EDTA, washed, resuspended in AIM-V medium and counted in a Guava EasyCyte mini. The IL-21 mAbs and an anti-bacterial negative control mAb (Ly128) were preincubated with rhIL-21 (Peprotech) in 100 μl AIM-V for 1 h at 37° C. and added to $2.5 \times 10^5$ transfected cells in 100 μl AIM-V in a 96-well cell culture plate with a final IL-21 concentration of 10 ng/ml. After 20 h incubation at 37° C. with 5% $CO_2$, 20 μl cell supernatant was mixed with 200 μl pNPP substrate (Mabtech, Nacka Strand, Sweden) in Maxisorp 96-well plates (Nunc, Roskilde, Denmark) and absorbance at 405 nm was measured.

MAb Blocking of rhIL-21 Receptor Interaction with PBMC

MAbs and rhIL-21 were preincubated as above and incubated in 200 μl cell culture medium with $3 \times 10^5$ PBMC/well in a cell culture plate at 37° C. with 5% $CO_2$ for 4 days. One hundred μl from each well was added to human IgG ELISpot plates and incubated for 6 h. The number of IgG-producing B cells was enumerated in a human IgG ELISpot (Mabtech) following the manufacturer's instructions.

Cell Stimulation for ELISA and ELISpot with or without Neutralizing mAb

PBMC were mixed with 5 μg/ml of Phytohemagglutinin (PHA; Oxoid AB, Malmö, Sweden), 13 ug/ml of CA (Greer, Lenoir, N.C., USA) or 7.2 LF/ml TT (Statens Serum Institut, Copenhagen, Denmark) or medium only. Cell concentrations were adjusted to $5 \times 10^6$ cells/ml. In some experiments, the biotinylated detection mAb MT3 was added to the cultures at 1 μg/ml. PBMC were incubated at 37° C. with 5% $CO_2$ for 40 h in 96-well cell culture plates (TPP, Nordic Biolabs, Tiby, Sweden) for preparation of cell supernatants for ELISA analysis (200 μl/well; $5 \times 10^6$ cells/ml). Alternatively, PBMC were incubated for 40 h directly in ELISpot wells (100 μl/well; $5 \times 10^6$ cells/ml).

ELISpot

The IL-21 ELISpot was performed essentially as described (Minang et al., 2008). Briefly, PVDF plates (Millipore) were EtOH treated and coated with mAb MT6 (10 μg/ml) at +4° C. PBMC were incubated with or without stimuli at 37° C. and 5% $CO_2$ for 40 h. The plates were then incubated with detection mAb MT3-biotin (1 μg/ml) for 2 h at RT, followed by streptavidin-horseradish peroxidase conjugate for 1 h at RT (Mabtech) and developed with precipitating TMB substrate for 15 min (Mabtech). ELISpot assays were set up in triplicates. A human IL-17A ELISpot kit (Mabtech) was run in parallel using the same protocol. Spots were counted using an ELISpot reader (iSpot Spectrum, AID, Strassberg, Germany). PBMC responding to antigen with >3× more spots and an increase of >10 spots compared to unstimulated PBMC from the same donor were considered positive.

ELISA

Maxisorp 96-well plates were coated for 16 h at 4° C. with 2 μg/ml capture mAb MT6 in 100 μl phosphate-buffered saline (PBS). Other assay steps were performed at RT using 100 μl/well except for washes between assay steps where 200 μl/well of PBS/0.1% Tween 20 were used. Coated wells were blocked for 1 h with incubation buffer (PBS with 0.05% Tween 20 and 0.1% bovine serum albumin). After incubation of rhIL-21 or supernatant for 2 h, detection mAb MT3-biotin at 1 µg/ml in incubation buffer was incubated 1 h followed by streptavidin horseradish peroxidase conjugate in incubation buffer for 1 h. The assay was developed with soluble TMB substrate (Mabtech) and stopped with 1 M $H_2SO_4$ and absorbance at 450 nm was measured. A human IL-17A ELISA kit (Mabtech) was run in parallel using the same protocol. Both ELISAs yielded a lowest detection limit below 10 µg/ml (mean background+3 SD in repeated tests) but the limit was set to 10 µg/ml due to low OD values (<0.1) at the lowest standard concentrations. PBMC responding to antigen with >2× higher levels and an increase of >10 pg/ml compared to unstimulated PBMC from the same donor were scored positive.

Statistics

The correlation between antigen-specific cytokine responses analyzed in different assays was assessed using Spearman's rank order correlation coefficient $r_s$. Values obtained with unstimulated cells were subtracted from those obtained with antigen-stimulated cells.

Results

The mAbs were tested for their capacity to neutralize IL-21 using transfected HEK cells responsive to IL-21 (FIG. 2A). MAb MT3, the selected detection mAb, efficiently inhibited IL-21-mediated activation (MT5 yielded identical results and is not shown in the figure) and MT4 had a weak inhibitory effect. In contrast, MT6 amplified the IL-21-mediated activation. The impact of the mAbs to IL-21 was therefore further analyzed with primary human PBMC expressing the IL-21 receptor naturally. Taking advantage of the fact that IL-21 activates memory B cells to become plasma cells (Ozaki et al., 2004; Ettinger et al., 2005), PBMC were incubated with IL-21 and mAbs and the number of IgG-secreting B cells were enumerated (FIG. 2B). MT3 (and MT5) again displayed a neutralizing effect whereas MT4 had no effect. MT6, however, displayed a reversed effect, compared to its effect on HEK cells, and neutralized the IL-21 activation of PBMC as efficiently as MT3. Similar results were obtained when IgG levels rather than IgG-secreting cells were measured (data not shown). Notably, when MT3 and MT6 were added together, they had a strong synergistic neutralizing effect on IL-21 activation of both HEK cells and PBMC (FIG. 3).

A possible explanation for the amplifying effect of MT6 alone on IL-21-activated HEK cells could be that IL-21 signaling occurs via antibody cross-linking and homodimerization of one of the chains in the IL-21 receptor, something that may be facilitated by its likely high expression in the transfected cells. Stimulation via receptor aggregation can be induced naturally via dimeric ligands or artificially via anti-receptor antibodies; in the case of the IL-4 receptor, sharing the common gamma chain with the IL-21 receptor, antibody-mediated homodimerization of the IL-4Rα chain was shown to lead to intracellular signaling (Kammer et al., 1996). In the current case, homodimerization might be induced by the MT6 antibody binding divalently to an epitope of IL-21 that is not involved in its interaction with the signaling chain. The fact that amplification was optimal at a certain ratio of MT6:rhIL-21 but decreased at higher concentrations where the antibody could be expected to bind monovalently (FIG. 2A), supports the hypothesis of MT6-induced homodimerization. The strong synergistic neutralizing effect of MT3 and MT6, in HEK cells and PBMC, further suggests that the two mAbs bind sites on IL-21 that interact with the different receptor chains and hence completely blocks the possibility of IL-21 signaling.

The IL-21 capture assays developed were used to analyze IL-21 secretion by PBMC from healthy subjects (n=24), stimulated polyclonally with PHA or with antigen (TT and CA). As shown in FIG. 4A, the ELISpot detected PHA-induced IL-21-secreting cells in PBMC from all donors and lower but positive responses to TT and CA in 50% and 58% of the donors, respectively. While the response to PHA was also readily measured in 23/24 donors in the ELISA, this assay completely failed to detect antigen-specific responses (FIG. 4B).

IL-17A analysis performed in parallel yielded comparable results as for IL-21 in the ELISpot with high responses to PHA and lower but positive responses to specific antigen; 38% of the donors responded to TT and 71% to CA (FIG. 4C). The ELISpot results for the two cytokines were also found to be positively correlated with regard to the antigen-specific responses ($r_s$ 0.78 for IT and 0.70 for CA; p<0.0001). Th17 cells are involved in the immune response to the fungus *C. albicans* (Jager and Kucharoo, 2010) and simultaneous production of both IL-17A and IL-21 by this cell type may explain the correlated response to CA antigen. A previous study has shown IL-17A responses to TT by PBMC at the mRNA level but failed to detect secreted protein by ELISA (Lenarczyk et al., 2000). The correlation between IL-17A and IL-21 seen herein suggests the involvement Th17 cells also in the response to TT vaccination.

In contrast to IL-21, IL-17A responses to TT and CA were also observed in ELISA with similar numbers of responders as seen in the ELISpot; 42% responding to TT and 75% to CA (FIG. 4D). The antigen-specific IL-17A responses measured by ELISpot and ELISA (FIGS. 4C & D) were positively correlated ($r_s$=0.82 for TT and 0.74 for CA, p<0.0001).

In view of the similar ELISpot results for IL-21 and IL-17A, the distinct discrepancy in the detection of these two cytokines in ELISA was somewhat surprising. An important difference between ELISpot and ELISA is that, in the ELISpot, the cytokine is captured by the coated mAbs immediately upon secretion whereas ELISA measures the net amount of cytokine in a culture supernatant after potential binding to soluble or cellular receptors. Such receptor consumption has previously been demonstrated for IL-4 which, similar to the findings here with IL-21, is notoriously difficult to detect by ELISA after antigen-specific ex vivo stimulation of PBMC, while more easily detected in ELISpot (Minang et al., 2008). This has been explained by an up-regulation of IL-4 receptors on various cells during stimulation (Renz et al. 1991; Carter and Swain, 1997) followed by an increased receptor consumption of secreted IL-4. In support of this, addition of IL-4 receptor-blocking antibodies during antigenic stimulation has been shown to result in increased levels of IL-4 in cell supernatants, thus demonstrating that even low frequencies of T cells can produce measurable levels of IL-4, provided receptor consumption is prevented (Ewen and Baca-Estrada, 2001).

To test whether receptor consumption could be a reason for the discrepancy between the IL-21 ELISA and ELISpot results, the experiments were repeated and PBMC (n=18) were incubated as before or in the presence of the anti-IL-21 neutralizing mAb MT3. The mAb was used biotinylated since non-labeled MT3 otherwise could interfere with the subsequent ELISA detection. As seen in FIGS. 5A and B, results from PBMC incubated without the neutralizing mAb were comparable to the initial results (FIGS. 4A & B) i.e.

antigen-specific responses were observed in ELISpot but not in ELISA. However, addition of mAb MT3 to the cell culture had a prominent effect on ELISA results (FIG. 5D) increasing the average PHA-induced levels of IL-21 nearly fourfold (from 890 pg/ml to 3400 pg/ml) and, more important, made previously non-detectable antigen-specific responses measurable. Addition of MT3 to unstimulated cells did not enhance IL-21 levels showing that the mAb prevents the loss of IL-21 rather than elevating the levels through non-specific induction. Although the antigen-induced IL-21 levels were in all cases low (<50 μg/ml) and failed to detect all donors scored as positive in the ELISpot, IL-21 levels detected by ELISA in supernatants made in the presence of neutralizing mAb correlated with ELISpot ($r_s$=0.70, p=0.0006 for TT and 0.61, p=0.074 for CA).

In ELISpot, the addition of blocking mAb to IL-21 had no effect on the response and cells incubated with or without blocking mAb displayed similar numbers of spots in response to antigens (FIGS. 5A and C) and were strongly correlated ($r_s$=0.95 for TT and 0.93 for CA, p<0.0001). The absence of any effect of the mAb in ELISpot resembles the use of an IL-4 receptor-blocking mAb that increased IL-4 levels but had no impact on ELISpot results (Ewen and Baca-Estrada, 2001).

Example 2—Epitope Mapping of Neutralizing Monoclonal Antibodies to Human IL-21

Background

In order to identify the sites on human IL-21 where the neutralizing mAbs MT3 and MT6 (Huang et al., 2014) bind, five human-mouse IL-21 chimeras were made. In each chimera, one region of the human IL-21 molecule was substituted with the corresponding mouse IL-21 residues. Since none of the mAbs display reactivity with mouse IL-21, substitution of a region comprising important residues in an epitope is likely to cause a loss of antibody binding. Critical regions in human IL-21 for the interaction with the IL-21 receptor chain have been shown to involve residues in the first (A) and third helical region (C) as well as the β-strand region (D) (Hamming et al., 2012). Regions comprising residues involved in the interaction with the common gamma chain have been shown to be the first (A) and last helical region (E) (Kang et al., 2010).

Methods

Recombinant IL-21 and Chimeras Used for Analysis of mAb Specificity

All genes were codon optimized, synthesized and cloned into the pIRES2-AcGFP1 plasmid (Clontech) by GenScript (Piscataway, N.J., USA). Recombinant human and mouse IL-21 and five human-mouse chimeric proteins were designed by replacing the four helical regions and the β-strand region with the corresponding residues from mouse IL-21; the substituted residues were 1-32 (helical chimera A), 33-57 (helical chimera B), 58-76 (helical chimera C), 77-100 (β-strand region D), 101-34 (helical chimera E). At the N terminus of all IL-21 variants, a 10 amino acid tag (DAEFRHDSGY; designated BAM) was recombinantly added. The BAM tag is recognized by mab bm-AbetaN (Mabtech). Proteins were expressed in transfected human HEK cells as previously described (Areström et al., 2012).

Confirmation of Expression of IL-21 Variants by Western Blot

Transfected cell lysate (20 μl) of each IL-21 variant and WT was mixed with NuPage LDS sample buffer (Invitrogen, Carlsbad, Calif., USA) and kept at 70° C. for 10 min. After that, samples were resolved under non-reducing conditions on NuPAGE 4-12% gradient Bis-Tris gels (Invitrogen) in a XCELL II Electrophoresis cell (Novex, San Diego, Calif., USA) using NuPage MOPS running buffer (Invitrogen). A pre-stained standard (SeeBlue Plus 2; Invitrogen) was included as reference. The proteins were transferred to 0.2 m pore size nitrocellulose membrane (Invitrogen) using a MiniTrans-Blot apparatus (Bio-Rad, Hercules, Calif., USA) with 20 mM Tris pH 8.6. Membranes were blocked for 1 h at room temperature with 4% fetal calf serum (FCS) and 0.1% Tween 20 in PBS. After washing with PBS, the membranes were incubated with 1 μg/ml of biotinylated anti-BAM mAb in PBS with 0.5% FCS. The membranes were washed and incubated for 1 h at room temperature with streptavidin-alkaline phosphatase (Mabtech) diluted 1:1000 in PBS, washed again and developed with BCIP/NBT Plus (Mabtech) for 5 min before being rinsed in tap water.

Sandwich ELISA to Assess mAb Reactivity with IL-21 Variants

Maxisorp 96-well plates (Nunc, Roskilde, Denmark) were coated for 16 h at 4° C. with 2 μg/ml of mAbs to IL-21 in 100 μl PBS. Other assay steps were at room temperature (RT), using 100 μl/well. Five washes using PBS with 0.1% Tween 20 were made between assay steps. After coating, wells were blocked for 1 h with incubation buffer (PBS with 0.05% Tween 20 and 0.1% bovine serum albumin). Cell lysate containing different IL-21 variants was serially diluted in incubation buffer and incubated for 2 h. After that, the biotinylated detection anti-BAM mAb, diluted in incubation buffer to 1 ug/ml, was incubated for 1 h and subsequently streptavidin-horseradish peroxidase conjugate (SA-HRP; Mabtech) in incubation buffer was added and incubated for 1 h. The assay was developed with 3,3',5,5'-tetramethylbenzidine substrate (Mabtech) and stopped with 1 M $H_2SO_4$ followed by absorbance measurement (450 nm) by an ELISA reader (Labsystems, Helsinki, Finland).

Results

The expression of all IL-21 variants in HEK cell lysate was confirmed by Western blot analysis (data not shown). Following that, mAb reactivity with human and mouse IL-21 as well as the IL-21 chimeras was assessed. In addition to MT3 and MT6, another anti-IL21 mAb (mAb 4) was analyzed. The mAbs displayed a comparable reactivity to wild type human IL-21 but no reactivity with mouse IL-21. With regard to the chimeric IL-21 variants, the mAbs differed in their reactivity and by identifying which chimeras that were poorly recognized by a certain antibody, the epitopes of the three mAbs could be identified. MAb MT3 lost reactivity with chimera D, MT6 lost reactivity with chimera B, C and E and mAb 4 lost reactivity with chimera A (FIG. 6). The fact that an antibody recognizes epitopes involving several regions is explained by the fact that antibodies often recognize non-linear epitopes with multiple regions that may be distant in the amino acid sequence but close in the tertiary structure of the folded protein.

CONCLUSION

The two antibodies MT3 and MT6 both recognize epitopes that comprise residues having been described to be involved in the interaction with the heterodimeric IL-21 receptor chains. The β-strand region (D) recognized by MT3 is one of the regions, together with the first and third helical regions that interact with the IL-21 receptor chain. MT6, on the other hand, displayed reactivity with several regions including the third helical region interacting with the IL-21 receptor chain as well as the last helical region that interacts with the common gamma chain. The mAbs, used together for neutralization, thus has the ability to interfere with binding to both receptor chains.

REFERENCES

Akamatsu, N., Yamada, Y., Hasegawa, H., Makabe, K., Asano, R., Kumagai, I., Murata, K., Imaizumi, Y., Tsukasaki, K., Tsuruda, K., Sugahara, K., Atogami, S., Yanagihara, K. and Kamihira, S., 2007, High IL-21 receptor expression and apoptosis induction by IL-21 in follicular lymphoma. Cancer Lett 256, 196-206.

Areström, I., Zuber, B., Bengtsson, T. and Ahlborg., 2012, Measurement of human latent transforming growth factor-β1 using a latency associated protein-reactive ELISA. J. Immunol. Methods 379, 23-29.

Brady, J., Carotta, S., Thong, R. P., Chan, C. J., Hayakawa, Y., Smyth, M. J. and Nutt, S. L., 2010, The interactions of multiple cytokines control NK cell maturation. J Immunol 185, 6679-88.

Carter, L. L. and Swain, S. L., 1997, Single cell analyses of cytokine production. Curr Opin Immunol 9, 177-82.

Dolff, S., Abdulahad, W. H., Westra, J., Doornbos-van der Meer, B., Limburg, P. C., Kallen-berg, C. G. and Bijl, M., 2011, Increase in IL-21 producing T-cells in patients with systemic lupus erythematosus. Arthritis Res Ther 13, R157.

Ettinger, R., Sims, G. P., Fairhurst, A. M., Robbins, R., da Silva, Y. S., Spolski, R., Leonard, W. J. and Lipsky, P. E., 2005, IL-21 induces differentiation of human naive and memory B cells into antibody-secreting plasma cells. J Immunol 175, 7867-79.

Ewen, C. and Baca-Estrada, M. E., 2001, Evaluation of interleukin-4 concentration by ELISA is influenced by the consumption of IL-4 by cultured cells. J Interferon Cytokine Res 21, 39-43.

Gelebart, P., Zak, Z., Anand, M., Dien-Bard, J., Amin, H. M. and Lai, R., 2009, Interleukin-21 effectively induces apoptosis in mantle cell lymphoma through a STAT1-dependent mechanism. Leukemia 23, 1836-46.

Hamming, O. J., Kang, L., Svensson, A., Karlsen, J. L., Rahbek-Nielsen, H., Paludan, S. R., Hjorth, S. A., Bondensgaard, K. and Hartmann, R., 2012, Crystal structure of interleukin-21 receptor (IL-21R) bound to IL-21 reveals that sugar chain interacting with WSXWS motif is integral part of IL-21R. J Biol Chem 287, 9454-60.

Holliger, P., Hudson, P. J., 2005, Engineered antibody fragments and the rise of single domains. Nature Biotechnology 23 (9), 1126-1136

Huang, J., Ehrnfelt, C., Paulie, S., Zuber, B. and Ahlborg, N., 2015, ELISpot and ELISA analyses of human IL-21-secreting cells: Impact of blocking IL-21 interaction with cellular receptors. J Immunol Methods 417, 60-6.

Jager, A. and Kuchroo, V. K., 2010, Effector and regulatory T-cell subsets in autoimmunity and tissue inflammation. Scand J Immunol 72, 173-84.

Kammer, W., Lischke, A., Moriggl, R., Groner, B., Ziemiecki, A., Gurniak, C. B., Berg, L. J. and Friedrich, K., 1996, Homodimerization of interleukin-4 receptor alpha chain can induce intracellular signaling. J Biol Chem 271, 23634-7.

Kang, L., Bondensgaard, K., Li, T., Hartmann, R. and Hjorth, S. A., 2010, Rational design of interleukin-21 antagonist through selective elimination of the gammaC binding epitope. J Biol Chem 285, 12223-31.

Korn, T., Bettelli, E., Gao, W., Awasthi, A., Jager, A., Strom, T. B., Oukka, M. and Kuchroo, V. K., 2007, IL-21 initiates an alternative pathway to induce proinflammatory T(H)17 cells. Nature 448, 484-7.

Lamprecht, B., Kreher, S., Anagnostopoulos, I., Johrens, K., Monteleone, G., Jundt, F., Stein, H., Janz, M., Dorken, B. and Mathas, S., 2008, Aberrant expression of the Th2 cytokine IL-21 in Hodgkin lymphoma cells regulates STAT3 signaling and attracts Treg cells via regulation of MIP-3alpha. Blood 112, 3339-47.

Lenarczyk, A., Helsloot, J., Farmer, K., Peters, L., Sturgess, A. and Kirldkham, B., 2000, Antigen-induced IL-17 response in the peripheral blood mononuclear cells (PBMC) of healthy controls. Clin Exp Immunol 122, 41-8.

Leonard, W. J., Zeng, R. and Spolski, R., 2008, Interleukin 21: a cytokine/cytokine receptor system that has come of age. J Leukoc Biol 84, 348-56.

Liu, S., Lizee, G., Lou, Y., Liu, C., Overwijk, W. W., Wang, G. and Hwu, P., 2007, IL-21 synergizes with IL-7 to augment expansion and anti-tumor function of cytotoxic T cells. Int Immunol 19, 1213-21.

Ma, J., Zhu, C., Ma, B., Tian, J., Baidoo, S. E., Mao, C., Wu, W., Chen, J., Tong, J., Yang, M., Jiao, Z., Xu, H., Lu, L. and Wang, S., 2012, Increased frequency of circulating follicular helper T cells in patients with rheumatoid arthritis. Clin Dev Immunol 2012, 827480.

Makitalo, B., Andersson, M., Arestrom, I., Karlen, K., Villinger, F., Ansari, A., Paulie, S., Thorstensson, R. and Ahlborg, N., 2002, ELISpot and ELISA analysis of spontaneous, mitogen-induced and antigen-specific cytokine production in cynomolgus and rhesus macaques. J Immunol Methods 270, 85-97.

Minang, J. T., Arestrom, I. and Ahlborg, N., 2008, ELISpot displays a better detection over ELISA of T helper (Th) 2-type cytokine-production by ex vivo-stimulated antigen-specific T cells from human peripheral blood. Immunol Invest 37, 279-91.

Moens, L. and Tangye, S. G., 2014, Cytokine-Mediated Regulation of Plasma Cell Generation: IL-21 Takes Center Stage. Front Immunol 5, 65.

Ozaki, K., Spolski, R., Ettinger, R., Kim, H. P., Wang, G., Qi, C. F., Hwu, P., Shaffer, D. J., Akilesh, S., Roopenian, D. C., Morse, H. C., 3rd, Lipsky, P. E. and Leonard, W. J., 2004, Regulation of B cell differentiation and plasma cell generation by IL-21, a novel inducer of Blimp-1 and Bcl-6. J Immunol 173, 5361-71.

Renz, H., Domenico, J. and Gelfand, E. W., 1991, IL-4-dependent up-regulation of IL-4 receptor expression in murine T and B cells. J Immunol 146, 3049-55.

Spolski, R. and Leonard, W. J., 2008, The Yin and Yang of interleukin-21 in allergy, autoimmunity and cancer. Curr Opin Immunol 20, 295-301.

Vallieres, F. and Girard, D., 2013, IL-21 enhances phagocytosis in mononuclear phagocyte cells: identification of spleen tyrosine kinase as a novel molecular target of IL-21. J Immunol 190, 2904-12.

van der Fits, L., Out-Luiting, J. J., van Leeuwen, M. A., Samsom, J. N., Willemze, R., Tensen, C. P. and Vermeer, M. H., 2012, Autocrine IL-21 stimulation is involved in the maintenance of constitutive STAT3 activation in Sezary syndrome. J Invest Dermatol 132, 440-7.

van Leeuwen, M. A., Lindenbergh-Kortleve, D. J., Raatgeep, H. C., de Ruiter, L. F., de Krijger, R. R., Groeneweg, M., Escher, J. C. and Samsom, J. N., 2013, Increased production of interleukin-21, but not interleukin-17A, in the small intestine characterizes pediatric celiac disease. Mucosal Immunol 6, 1202-13.

Vaughan, T. J., Osbourn, J. K., Tempest, P. R., 1998, Human antibodies by design. Nature Biotechnology 16 (6), 35-539

Winter, G., Harris, W. J., 1993, Humanized antibodies. Immunology Today 14 (6), 243-246

The invention claimed is:

1. A composition for inhibition and/or neutralization of interleukin-21 (IL-21) mediated activation of human cells comprising:
   (i) a first agent directed to a first epitope of IL-21, the first agent being an IL-21 binding antibody or antibody fragment thereof, comprising the six complementarity determining regions (CDRs) of monoclonal antibody MT6 produced by the cell line MT21.6G deposited with the American Type Culture Center (ATCC) under Patent Deposit Number PTA-126046, and
   (ii) a second agent directed to a second epitope of IL-21, the second agent being an IL-21 binding antibody or antibody fragment thereof, selected from the group consisting of an IL-21 binding antibody, or fragment thereof, comprising the six CDRs of monoclonal antibody MT3 produced by the cell line MT21.3m deposited with the ATCC under Patent Deposit Number PTA-126045, and an IL-21 binding antibody, or fragment thereof, comprising the six CDRs of monoclonal antibody MT5 produced by the cell line MT21.5 deposited with the ATCC under Patent Deposit Number PTA-126568,
   wherein said composition is formulated with at least one pharmaceutically acceptable excipient.

2. The composition according to claim 1, wherein said first and/or second agent comprises a fully human, chimeric or humanized antibody or a fragment of a fully human, chimeric or humanized antibody.

3. The composition according to claim 1, wherein said second agent comprises the six CDRs of the monoclonal antibody MT3 produced by the cell line MT21.3m deposited with the ATCC under Patent Deposit Number PTA-126045.

4. The composition according to claim 3, wherein (i) said first agent is a human, chimeric or humanized antibody or antibody fragment thereof, and (ii) said second agent is a human, chimeric or humanized antibody or antibody fragment thereof.

5. The composition according to claim 4, wherein (i) said first agent is a chimeric or humanized antibody or antibody fragment thereof, and (ii) said second agent is a chimeric or humanized antibody or antibody fragment thereof.

6. The composition according to claim 1, wherein said second agent comprises the six CDRs of the monoclonal antibody MT5 produced by the cell line MT21.5 deposited with the ATCC under Patent Deposit Number PTA-126568.

7. The composition according to claim 5, wherein (i) said first agent is a human, chimeric or humanized antibody or antibody fragment thereof, and (ii) said second agent is a human, chimeric or humanized antibody or antibody fragment thereof.

8. The composition according to claim 5, wherein (i) said first agent is a chimeric or humanized antibody or antibody fragment thereof, and (ii) said second agent is a chimeric or humanized antibody or antibody fragment thereof.

9. The composition according to claim 1, wherein said first and second agents are is in the form of a bispecific antibody (bisAb), or fragment thereof, being able to bind both the first and second epitopes of IL-21.

10. The composition according to claim 1, wherein said first and/or second agent is a Fab fragment, F(ab')2 fragment, single chain Fv fragment or monovalent IgG.

11. The composition according to claim 1, wherein said first epitope comprises:
    the third helical region interacting with the IL-21 receptor chain, and
    the last helical region that interacts with the common gamma chain.

12. The composition according to claim 1, wherein said second epitope comprises:
    the β-strand region (D).

13. A kit for inhibition and/or neutralization of interleukin-21 (IL-21) mediated activation of human cells comprising:
    (i) a first agent directed to a first epitope of IL-21, the first agent being an IL-21 binding antibody, or a fragment thereof, comprising the six complementarity determining regions (CDRs) of monoclonal antibody MT6 produced by the cell line MT21.6G deposited with the American Type Culture Center (ATCC) under Patent Deposit Number PTA-126046, and
    (ii) a second agent directed to a second epitope of IL-21, the second agent being an IL-21 binding antibody, or fragment thereof, selected from the group consisting of an IL-21 binding antibody, or fragment thereof, comprising the six CDRs of monoclonal antibody MT3 produced by the cell line MT21.3m deposited with the ATCC under Patent Deposit Number PTA-126045, and an IL-21 binding antibody, or fragment thereof, comprising the six CDRs of monoclonal antibody MT5 produced by the cell line MT21.5 deposited with the ATCC under Patent Deposit Number PTA-126568,
    wherein said first and second agents are each formulated with at least one pharmaceutically acceptable excipient.

14. A method of inhibition and/or neutralization of interleukin-21 (IL-21) mediated activation of human cells in a subject diagnosed with a disease associated with IL-21 production comprising the steps of administering to the subject (i) a first agent directed to one epitope of IL-21, the first agent being an IL-21 binding antibody, or a fragment thereof, comprising the six complementarity determining regions (CDRs) of monoclonal antibody MT6 produced by the cell line MT21.6G deposited with the American Type Culture Center (ATCC) under Patent Deposit Number PTA-126016 accession number, and (ii) a second agent directed to a second epitope of IL-21, the second agent being an IL-21 binding antibody, or fragment thereof, selected from the group consisting of an IL-21 binding antibody, or fragment thereof, comprising the six CDRs of monoclonal antibody MT3 produced by the cell line MT21.3m deposited with the ATCC under Patent Deposit Number PTA-126045, and an IL-21 binding antibody, or fragment thereof, comprising the six CDRs of monoclonal antibody MT5 produced by the cell line MT21.5 deposited with the ATCC under Patent Deposit Number PTA-126568, wherein said administration is simultaneous or sequential, and wherein the combined administering of said first and second agents has a synergistic neutralizing effect on IL-21 activation of cells for the treatment of a disease associated with IL-21 production.

15. The method according to claim 14, wherein the disease associate with IL-21 production is a lymphoma or is an immune-related disease selected from inflammatory disease and autoimmunity.

16. The method according to claim 14, wherein the immune-related disease is selected from the group consisting of systemic lupus erythematosus, rheumatoid arthritis, celiac disease, osteoarthritis, psoriatic arthritis, ankylosing spondylitis, transplant rejection, inflammatory bowel disease, psoriasis, cystic fibrosis and Crohn's disease.

17. The method according to claim 14, wherein the first and second agents are administered simultaneously.

18. The method according to claim 14, wherein the first and second agents are administered sequentially.

19. The method according to claim 14, wherein said second agent comprises the six CDRs of the monoclonal antibody MT3 produced by the cell line MT21.3m deposited with the ATCC under Patent Deposit Number PTA-126045.

20. The method according to claim 14, wherein said second agent comprises the six CDRs of the monoclonal antibody MT5 produced by the cell line MT21.5 deposited with the ATCC under Patent Deposit Number PTA-126568.

\* \* \* \* \*